United States Patent [19]

Palmer

[11] Patent Number: 5,174,302
[45] Date of Patent: Dec. 29, 1992

[54] VARIABLE RADIOPACITY GUIDEWIRE WITH SPACED HIGHLY RADIOPAQUE REGIONS

[75] Inventor: Matthew A. Palmer, Miami, Fla.

[73] Assignee: Cordis Corporation, Miami, Fla.

[21] Appl. No.: 621,867

[22] Filed: Dec. 4, 1990

[51] Int. Cl.⁵ .............................................. A61B 5/00
[52] U.S. Cl. ................................... 128/772; 128/657; 604/164; 604/280
[58] Field of Search ................. 128/657, 772, 658; 604/95, 164, 280, 282; 606/192

[56] References Cited

U.S. PATENT DOCUMENTS

| | | | |
|---|---|---|---|
| 3,906,938 | 9/1975 | Fleischhacker | 128/772 |
| 4,538,622 | 9/1985 | Samson et al. | 128/772 |
| 4,545,390 | 10/1985 | Leary | 128/772 |
| 4,684,363 | 9/1987 | Ari et al. | 604/98 |
| 4,793,359 | 12/1988 | Sharrow | 128/658 |
| 4,821,722 | 4/1989 | Miller et al. | 128/344 |
| 4,846,186 | 7/1989 | Box et al. | 128/657 |
| 4,922,924 | 5/1990 | Gambale et al. | 128/772 |
| 4,964,853 | 10/1990 | Sugiyama et al. | 604/96 |
| 5,002,532 | 3/1991 | Gaiser et al. | 604/101 |

Primary Examiner—Stephen C. Pellegrino
Assistant Examiner—Guy V. Tucker
Attorney, Agent, or Firm—Watts, Hoffmann, Fisher & Heinke

[57] ABSTRACT

A guidewire for use in inserting diagnostic and therapeutic catheters. The guidewire has an initial uniform diameter segment that is coated with a polymerized silicone along a majority of its length. This core section tapers along a uniform portion to a second constant diameter segment surrounded by a flexible spring tip. The spring tip is banded to define portions that are highly radiopaque and portions that are much less radiopaque to X-radiation. This allows post angioplasty X-ray imaging of the blood vessel without removal of the guidewire.

12 Claims, 2 Drawing Sheets

VARIABLE RADIOPACITY GUIDEWIRE WITH SPACED HIGHLY RADIOPAQUE REGIONS

TECHNICAL FIELD

The present invention relates to a flexible elongated guidewire used to position a catheter within a patient.

BACKGROUND ART

Percutaneous Coronary Angioplasty is a therapeutic medical procedure that can increase blood flow through the coronary artery. It can sometimes be used as an alternative to coronary by-pass surgery. An elongated catheter having a deflated balloon at its distal end is guided through a patient's cardiovascular system to the coronary artery of the heart. The balloon is inflated to compress deposits that have accummulated along the inner walls of the coronary artery to widen the artery lumen and increase blood flow.

A known technique for positioning the balloon catheter uses an elongated guidewire that is inserted into the patient and routed through the cardiovascular system as guidewire progress is viewed on an x-ray imaging screen.

The path the guidewire follows as it is inserted is tortuous. The distal tip is flexible to avoid damaging inner walls of the blood vessels that the guidewire tip contacts along the tortuous path. The distal tip is often pre-bent to a desired configuration so that the guidewire can be inserted into the branching blood vessels along the path. When the tip is pre-bent the physician must be able to orient the tip so it can be pushed into these branching blood vessels.

Representative prior art patents that disclose flexible, elongated guidewires are U.S. Pat. No. 4,545,390 to Leary, U.S. Pat. No. 4,538,622 to Samson et al. and U.S. Pat. No. 3,906,938 to Fleischhacker. U.S. Pat. No. 4,846,186 to Box et al. is assigned to the assignee of the present application and is incorporated herein by reference.

One problem with currently available guidewires concerns the visibility of the guidewire. If the guidewire is fully opaque on a viewing screen, it can hinder viewing of post angioplasty angiograms used in studying the effects the angioplasty procedure had on the treated vessel. Guidewires that have only an opaque tip do not adequately depict the arterial path on the viewing monitor.

U.S. Pat. No. 4,922,924 to Gambale et al. concerns a guidewire for use with a catheter. The guidewire includes a coil assembly that is formed from a highly radiopaque coil and a non-radiopaque coil, arranged in bifilar arrangement to define a moderate radiopacity guidewire section.

DISCLOSURE OF THE INVENTION

The present invention relates to an elongated flexible guidewire designed for insertion into blood vessels to aid in positioning a catheter within a subject.

An elongated flexible guidewire constructed in accordance with the invention includes a core wire having a first diameter portion extending to a distal portion of the guidewire where the core wire tapers to a second, lesser diameter portion shorter than said first diameter portion. A flexible coiled wire spring is attached at either of its ends to the core wire and spaced from the core wire along the lesser diameter portion of said core wire. The flexible coiled wire spring has highly radiopaque portions spaced by less opaque portions to increase the visibility of said guidewire at spaced locations along the guidewire's distal end.

In accordance with a preferred construction the flexible coil spring is constructed from stainless steel and the highly radiopaque portions are constructed from a platinum/tungsten alloy that is visible when viewed on an X-ray viewing monitor.

As the stainless steel wire is wound, the pitch of the winding is altered to leave gaps between adjacent coils. The highly opaque wire coils are interleaved into these gaps before the spring is mounted onto the core wire. The extreme distal tip of the guidewire is then formed by welding the distal end of the spring to a flattened portion of the core wire.

From the above it is appreciated that one object of the invention is a flexible guidewire having improved visibility due to its banded distal construction. This and other objects, advantages and features of the invention will become better understood from a detailed description of the invention which is described in conjunction with the accompanying drawings.

BEST MODE FOR CARRYING OUT THE INVENTION

Figures 1, 3:
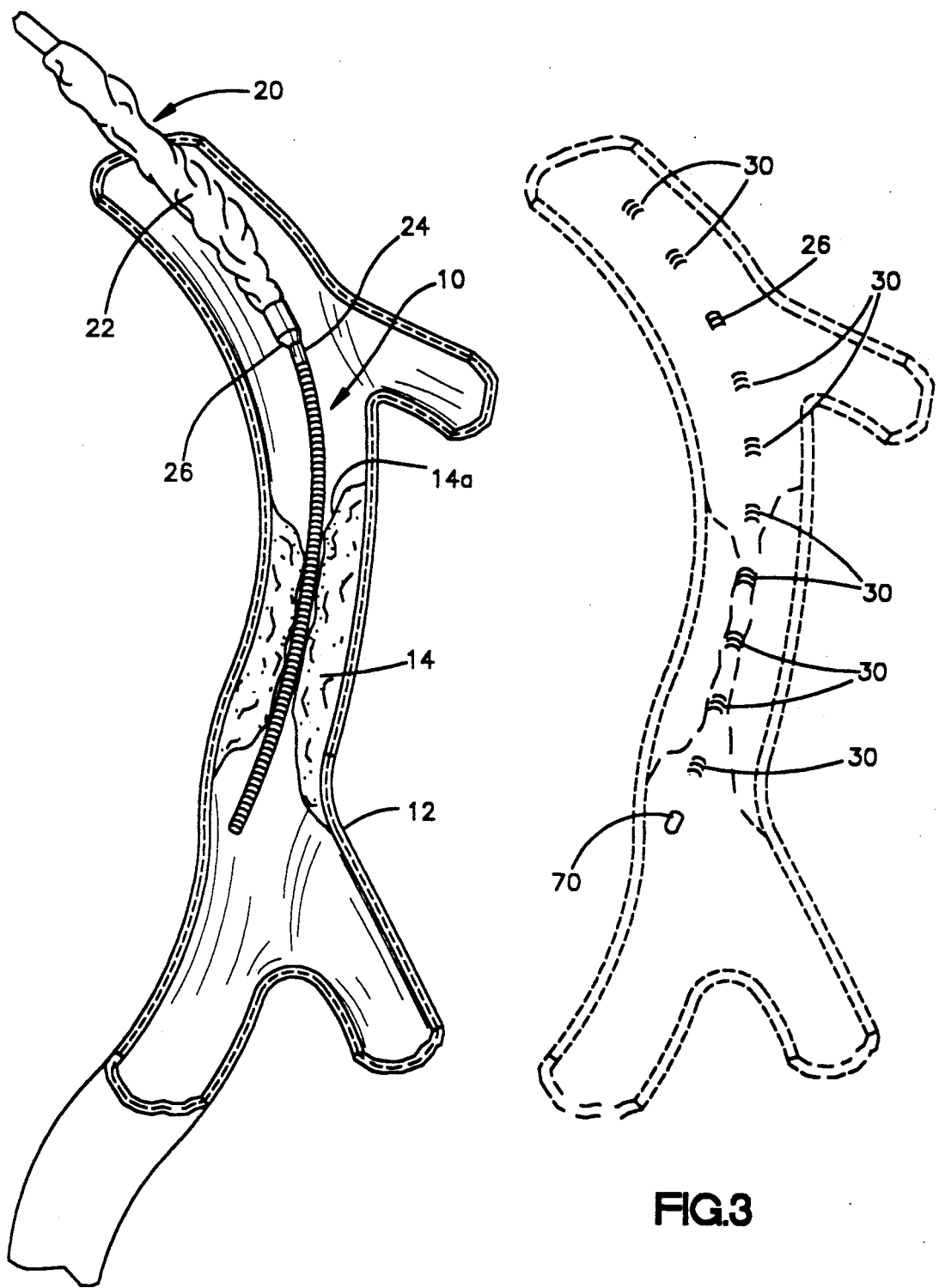
FIG. 1 is a diagrammatic view showing a blood vessel that has been occluded with deposits along an inner wail and shows the positioning of a flexible guidewire within the blood vessel.
FIG. 3 is a view of a flexible guidewire constructed in accordance with the invention as it appears when viewed on a fluoroscopic examining screen.

Turning now to the drawings, FIG. 1 illustrates a distal portion of a flexible, small diameter guidewire 10 that can be guided through a patient's cardiovascular system. A distal end of the guidewire is approaching a region in a blood vessel 12 having occlusions 14 which have restricted blood flow through the blood vessel 12. The guidewire 10 is long enough to be routed from a patient entry point through the patient to the obstructed blood vessel region. In a preferred embodiment the guidewire is 175 cm. long (approximately 69 inches). As the guidewire 10 is inserted along the tortuous path to the obstructed blood vessel region, an attending physician conducting the procedure monitors progress of the guidewire 10 on a viewing screen.

The FIG. 1 depiction illustrates use of a guidewire for routing a balloon catheter 20 to the vicinity of the obstructions 14. The balloon catheter 20 includes a passageway or lumen that extends from a proximal location outside the patient to a distally located balloon 22. Fluid is routed into the catheter through this lumen to inflate the balloon 22. A distal tip portion 24 of the catheter 20 includes a marker band 26 to aid the attending physician in monitoring balloon catheter progress as it is positioned within the patient. A second, center passageway or lumen in the catheter 20 has a diameter sufficient to accommodate the guidewire 10 so that once the guidewire is properly positioned the catheter 20 can be slid over the guidewire.

The distal tip portion of the guidewire 10 is flexible and can be bent to a predetermined configuration to facilitate routing the guidewire 10 along the cardiovascular system to the blood vessel 12. The pre-bent tip can be reoriented by the physician. Torques applied to the proximal end of the guidewire are transmitted along the length of the guidewire and re-orient the distal tip to point in a desired direction.

In use, a distal end of the guidewire 10 is routed through a narrow passageway 14a in the obstruction 14 and the balloon catheter 20 slipped over the guidewire until the balloon 22 bridges the region 14 of obstructions within the blood vessel 12. The balloon 22 is then inflated and the balloon's outer surface contacts the obstruction 14. The inner walls of the obstruction 14 are compressed and a wider lumen or passageway created in the blood vessel 12.

As described in detail below, the guidewire 10 is constructed so that bands 30 (FIG. 3) of high radiopaqueness appear when the blood vessel 12 is monitored on a viewing screen. The bands 30 are separated at a fixed distance thereby giving a reference length. The opacity of the bands 30 can be varied and in such an embodiment, the opacity of the bands 30 diminishes at the distal or working end of the guidewire 10. This would allow adequate tracing of the guidewire while minimizing interference with a post procedure angiogram.

Figure 2:
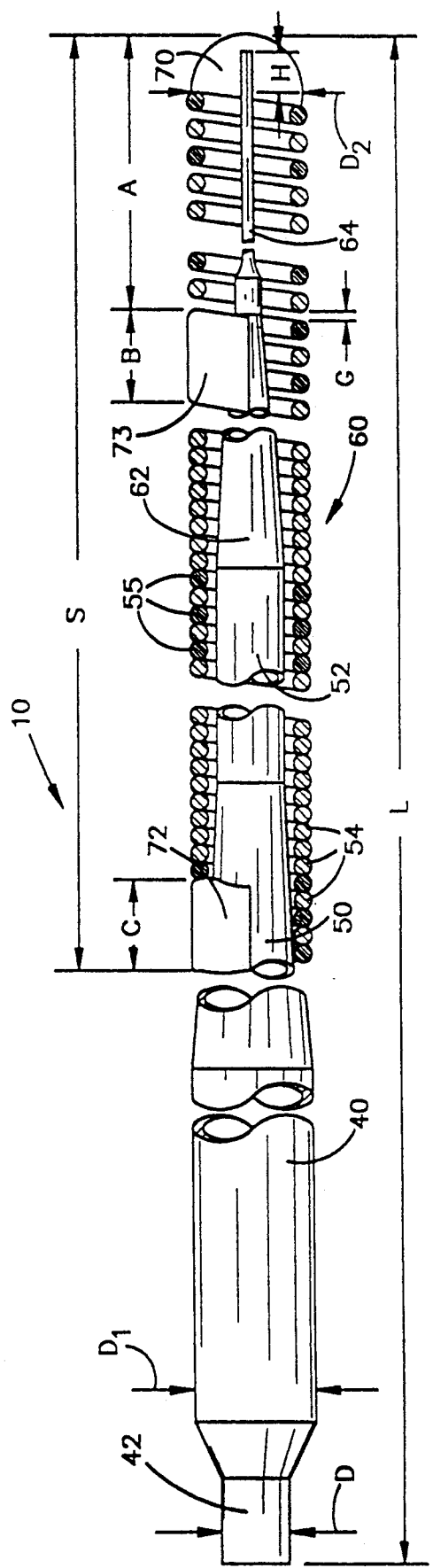
FIG. 2 is an elevation segmented view of a flexible guidewire constructed in accordance with the invention.

Turning now to FIG. 2, the guidewire 10 is seen to include a center stainless steel wire core 40 having a first uniform diameter $D_1$, extending well over half the length "L" of the guidewire. To improve the depiction of details of the distal portion of the guidewire 10, this uniform diameter elongated portion has been sectioned and a major portion of its length deleted from FIG. 2.

The total length of the uniform diameter portion 40 is approximately 148 cm. of the total guidewire length of 175 cm. A proximal tapered segment 42 of the core 40 having a diameter D is exposed and a thin silicone polymerized coating covers the rest of the guidewire 10. The exposed proximal segment can be more easily grasped by the attending physician and also allows a clamping device to be used to rotate the guidewire's proximal end.

The core 40 tapers along a segment 50 in a uniform manner to a second reduced diameter portion 52. At the point the core begins to taper, the core 40 is covered by a coiled wire spring 60. The core 40 again tapers in a uniform manner along a segment 62. An extreme distal segment 64 of the core 40 is flattened and surrounded by a less tightly coiled portion of the spring 60. This distal segment of the guidewire 10 can be pre-bent to a particular configuration by the attending physician to facilitate insertion of the guidewire within the subject.

At the extreme distal tip portion of the guidewire 10, a weld 70 attaches the distal portion of the spring 60 to the flattened portion 64 of the core. The weld defines a smooth hemispherical bead which does not damage the inner lining of the blood vessels as the tip comes in contact with those linings. The polymerized silicone is applied to a thickness of less than 0.0005 inch by dipping the guidewire, including the spring 60 and distal tip into a liquid bath.

Table I below provides representative dimensions for a preferred guidewire construction and tolerances for those dimensions.

TABLE I

| Dimension (FIG. 2) | Nominal (Inches) | Tolerance |
|---|---|---|
| L | 68.90 | ±.39 |
| A | 1.00 | ±.10 |
| B | .04 | ±.02 |
| C | .15 | ±.08 |
| D | .0090 | +.0003 / −.0000 |
| $D_1$ | .0130 | ±.0003 |
| $D_2$ | .0143 | ±.0000 / −.0003 |
| G | .0015 MAX. / .0010 MIN. | |
| H | .003 MIN. | |
| S | 12.00 | ±.30 |

The preferred spring 60 is a stainless steel wire. The spring is closely packed so that along the core segments 50, 52 adjacent coils 54 of the spring 60 touch each other. The coils 54 are less tightly packed at fixed distances to define gaps or spaces. These gaps of loosely wound coils then have coils 55 of a platinum/tungsten wire alloy having a percent by weight of 92% platinum and 8% tungsten wound in among the stainless steel coils 54 to create intermittent bands or regions of high radiopaqueness. If it is desired to have the shades of the bands 30 lighter, a different density alloy is utilized.

The spring 60 is soldered to the core 40 using Utectic Brand No. 157 Silver Base, Cadmium Free, Low Temperature, Surgical Grade Solder. One solder connection 72 is at the proximal end of the spring 60 and a second connection 73 joins the core 40 to the spring 60 when adjacent coils are spaced apart rather than touching. The core 40 is constructed from a uniform diameter stainless steel wire which is centerless ground along the tapered segment 50 to the reduced diameter segment 52 and again ground along the tapered segment 62. The flattened portion 64 is formed by rolling or stamping a uniform diameter core portion having an initial diameter of 0.0025 inch which when flattened by a die, results in 0.0012 inch thick by 0.0045 inch wide flattened portion that "bulges" outward on two sides.

The guidewire 10 depicted in FIG. 2 is particularly suited for insertion into small diameter blood vessels and can be used, for example, for positioning a balloon in a bridging relationship within the coronary artery.

FIG. 3 illustrates the image of the guidewire 10 which a physician would see while using the guidewire during angioplasty. A band 26 marks the catheter balloon to aid the attending physician in monitoring its progress within the blood vessel 12. Unlike a fully radiopaque guidewire, the bands 30 are visible at spaced locations to aid the physician during the angioplasty while not interfering with a post procedure angiogram. The bands 30 are equally spaced to provide a reference for the physician with regard to positioning the guidewire 10 within the blood vessel 12.

The dimensions shown in Table I are for a preferred embodiment of the invention for use in small diameter blood vessels. These dimensions are representative of this use and are not intended to limit the invention, but rather define a small diameter guidewire whose characteristics are particularly advantageous. It is the intent, however, that the invention include all modifications and/or alterations from the disclosed dimensions and design falling within the spirit or scope of the appended claims.

I claim:

1. An elongated flexible guidewire for insertion within a subject comprising:
   a) a core wire having a first portion extending to a distal portion of the guidewire where the core wire tapers along a tapered portion to a lesser diameter;
   b) a flexible coiled wire spring attached at either of its ends to the core wire and spaced from the core wire along at least a segment of the distal portion of said guidewire; and
   c) a plurality of highly radiopaque marker coil segments interwoven with the flexible coiled wire spring at spaced predetermined fixed distances along the distal portion to increase the fluoroscopic visibility of said guidewire at spaced apart locations along the guidewire's distal portion.

2. The flexible guidewire of claim 1 wherein the highly radiopaque marker coil segments consists of a platinum/tungsten alloy.

3. The flexible guidewire of claim 2 wherein each highly radiopaque marker coil segment has a controlled concentration of radiopaque constituents to provide controlled radiopaqueness.

4. The guidewire of claim 1 wherein a distal end portion of said flexible guidewire is a highly radiopaque material.

5. An elongated flexible guidewire comprising:
   a) a core wire having a first diameter portion extending to a distal portion of the guidewire where the core wire tapers to a second, lesser diameter portion shorter than said first diameter portion;
   b) a flexible coiled wire comprised of a relatively low radiopaque material and attached at either of its ends to the core wire; said flexible coiled wire being tightly wound in intermittent regions to provide low radiopaque regions and loosely wound in other intermittent marker regions to allow for other marker coils to be interwoven with the flexible coiled wire; and
   c) highly radiopaque marker coils interwoven at the intermittent marker regions of the coiled wire spring to provide spaced regions of high radiopaqueness.

6. The guidewire of claim 5 wherein said highly radiopaque marker coils are constructed of platinum/tungsten alloy wire of varying densities interwoven among the flexible coiled wire whereby each region of radiopaqueness varies in intensity to allow for proper tracing and referencing when said guidewire is in use.

7. The guidewire of claim 5 wherein said tighly wound intermittent regions are of a fixed length to provide a length reference when said guidewire is in use.

8. An elongated flexible guidewire for insertion within a subject comprising:
   a) a core wire having a first portion extending to a distal portion of the guidewire where the core wire tapers along a tapered portion to a second, lesser diameter;
   b) a flexible coiled wire spring attached at either of its ends to the core wire and spaced from the core wire along a segment of the distal portion of said guidewire; and
   c) three or more of highly radiopaque marker bands attached to the guidewire at spaced predetermined fixed distances along the distal portion of the guidewire to increase the visibility of said guidewire at spaced apart locations.

9. The elongated flexible guidewire of claim 8 wherein the flexible coiled wire spring is attached to an extreme distal end of said core wire and provides a highly visible rounded tip to said guidewire.

10. An elongated flexible guidewire comprising:
    a) a core wire having a first diameter portion extending to a distal portion of the guidewire where the core wire tapers to a second, lesser diameter portion shorter than said first diameter portion;
    b) a flexible coiled wire comprised of a relatively low radiopaque material and attached at either of its ends to the core wire; said flexible coiled wire being tightly wound in intermittent regions to provide low radiopaque regions and loosely wound in three or more other intermittent marker regions to allow for other marker coils to be interwoven with the flexible coiled wire; and
    c) three or more highly radiopaque marker coils interwoven at the intermittent marker regions of the coiled wire spring to provide spaced regions of high radiopaqueness.

11. The elongated flexible guidewire of claim 10 wherein the tightly wound intermittent regions of said flexible coil wire separate the loosely wound regions by a fixed length to provide a length reference as the elongated flexible guidewire is viewed from outside a subject.

12. The elongated flexible guidewire of claim 10 wherein the flexible coiled wire is attached to an extreme distal end of said core wire and provides a highly visible rounded tip to said guidewire.

* * * * *